United States Patent [19]

Niwa et al.

[11] Patent Number: 5,102,985
[45] Date of Patent: Apr. 7, 1992

[54] PROCESS FOR THE FORMATION OF INTRAMOLECULAR DISULFIDE BRIDGE IN A POLYPEPTIDE

[75] Inventors: Mineo Niwa, Muko; Masakazu Kobayashi, Takarazuka; Yoshinori Ishii, Suita; Ikuo Ueda, Toyonaka, all of Japan

[73] Assignee: Fujisawa Pharmaceutical Co., Ltd., Osaka, Japan

[21] Appl. No.: 417,323

[22] Filed: Oct. 4, 1989

[30] Foreign Application Priority Data

Oct. 7, 1988 [JP] Japan .............................. 63-254530

[51] Int. Cl.$^5$ .............................................. C07K 7/10
[52] U.S. Cl. .................................. 530/311; 530/324; 530/345; 530/351

[58] Field of Search ................. 530/345, 311, 324, 351

[56] References Cited

U.S. PATENT DOCUMENTS

| | | | |
|---|---|---|---|
| 4,530,787 | 7/1985 | Shaked et al. | 530/345 |
| 4,656,248 | 4/1987 | Kalbag et al. | 530/345 |
| 4,835,254 | 5/1989 | DiMarchi et al. | 530/345 |
| 4,960,868 | 10/1990 | Canosi et al. | 530/345 |

*Primary Examiner*—Lester L. Lee
*Attorney, Agent, or Firm*—Oblon, Spivak, McClelland, Maier & Neustadt

[57] ABSTRACT

The cysteine-containing polypeptide is oxidized with hydrogen peroxide to produce the biologically active polypeptide having the intramolecular disulfide bridge.

5 Claims, No Drawings

PROCESS FOR THE FORMATION OF INTRAMOLECULAR DISULFIDE BRIDGE IN A POLYPEPTIDE

The present invention relates to a process for the formation of intramolecular disulfide bridge in a polypeptide.

More particulary, it relates to a process for the formation of intramolecular disulfide bridge in a cysteine-containing polypeptide by using hydrogen peroxide.

There are some known processes for the formation of intramolecular disulfide bridge between two cysteine residues in a polypeptide. Most representative such known processes include air-oxidation process [see B.B.R.C. 119, 131 (1984)], iodine-oxidation process [see "peptide Chemistry" 229-234 (1984)], potassium ferricyanide-oxidation process [see "Peptide Chemistry" 241-246 (1984)].

But these processes have some disadvantages respectively as follows.

In the air-oxidation process, the proceeding speed of the reaction progress itself is very slow, and especially, it hardly proceeds under denaturing condition, such as in a highly concentrated salt or urea-aqueous solution of polypeptide. In the iodine-oxidation process, tyrosine residue(s) in a polypeptide may be disadvantageously iodinated. Lastly, in the potassium ferricyanide-oxidationprocess, it produces the problem of enviromental pollution, since the resultant waste water contains $CN^-$.

While, it is well known to use hydrogen peroxide as an oxidizing agent for an organic compound. On the contrary, concerning a polypeptide, it is generally recognized that hydrogen peroxide does not oxidize mercapto group of the polypeptide such as enzyme to give intramolecular disulfide bridge [European J. Biochem. 10 (1969) 533-538]. Further, it is generally believbed that methionine residue(s) which may be co-exist in a cysteine-containing polypeptide will be surely oxidized to give methionine sulfoxide residue(s), if the above polypeptide is forced to be oxidized with hydrogen peroxide. From these reasons, hydrogen peroxide-oxidation process is considered as an inappropriate one to produce the biologically active polypeptide.

Accordingly, an object of the present invention is to provide a process which easily and certainly gives the biologically active polypeptide by forming the intramolecular disulfide bridge in a polypeptide using hydrogen peroxide, even though methionine residue(s) co-exists in a polypeptide.

The inventors of the present invention have studied to establish the new process to form the intramolecular disulfide bridge by oxidizing the cysteine-containing polypeptide which is prepared through recombinant DNA technology or organic synthesis.

In the present invention, the methionine residue(s) which may be co-exist in a polypeptide is not or little oxidized, contrary to the general expectation, during the course to form the intramolecular disulfide bridge by oxidizing two cysteine residues with hydrogen peroxide.

The process of the present invention is carried out by oxidizing the cysteine-containing polypeptide or both cysteine- and methionine-containing polypeptide with hydrogen peroxide to produce efficiently the biologically active polypeptide which has intramolecular disulfide bond.

The cysteine-containing polypeptide or both cysteine- and methionine-containing polypeptide of the present invention includes so-called reduced form of polypeptide which requires the formation of intramolecular disulfide bridge in order to recover the biological activity, Such polypeptide may be prepared through recombinant DNA technology or organic synthesis.

The representative examples of the said polypeptide include reduced form of α-hANP (human atrial natriuretic peptide), reduced form of somatostatin, reduced form of IL-2 (interleukin-2), reduced form of TNF (tomor necrosis factor), and so on.

The reaction of the present invention is usually carried out at pH 6~11, preferably at alkaline pH, and more preferably around pH 8~11. The molar ratio of hydrogen peroxide and polypeptide is at least stoichiometric and, for example, is selected within the range of (1:1)~(100:1), preferably (1:1)~(3:1).

The reaction of the present invention is preferably carried out in the solution wherein the polypeptide is dissolved in suitable buffer solution.

The reaction is usually carried out at ambient temperature.

The following examples are given only for the purpose of illustrating the present invention in more detail.

EXAMPLE 1

Reduced form of α-hANP (10 mg) was dissolved in 10 mM sodium phosphate buffer solution (9.3 ml, pH 8.5) containing 0.5M sodium chloride, and was added 10 mM aqueous hydrogen peroxide (0.66 ml) thereto. The reaction mixture was allowed to stand for 10 minutes at ambient temparature. After reaction was over, oxidized form of α-hANP (natural form of α-hANP containing disulfide bond) in the reaction mixture was quantitatively determined with reversed phase high pressure liquid chromatography (RP-HPLC). The yeild of oxidized form of α-hANP was 9.6 mg (96%) and that of α-hANP wherein methionine residue was also oxidized [Met (0)-α-hANP] was only 0.15 mg.

COMPARATIVE EXAMPLE 1

Reduced form of α-hANP (110 mg) was dissolved in 10 mM sodium phosphate buffer (50 ml, pH 8.5) containing 0.5M sodium chloride. The reaction mixture was allowed to stand overnight at ambient temparature, and then the resultant oxidized form of α-hANP was quantitatively determined with RP-HPLC. The yield of oxidized form of α-hANP was 33.8 mg (30.7%). The most part (68.6 mg) of raw material was recovered as unchanged.

The experimental condition of RP-HPLC:

| Culumn | YMC AP-302 ODS (φ4.6 × 150 mm) |
|---|---|
| Solvent | A 20% $CH_3CN$ in 0.01 MTFA B 60% $CH_3CN$ in 0.01 MTFA |
| Elution | A → B 40 minutes |
| Fluid speed | 1.0 ml/min |
| Detection | 214 nm |

EXAMPLE 2

Reduced form of α-hANP (0.5 mg) was dissolved in 10 mM tris-HCl buffer (1 ml, pH 8.0) containing 6M guanidine hydrochloride, and 10 mM aqueous hydrogen peroxide (60 μl) was added thereto. The reaction mixture was allowed to stand for 10 minutes at ambient temparature. The reaction mixture was determined for RP-HPLC in the same manner as Example 1. The yeild of oxidized form of α-hANP was 0.45 mg (90%) and the yield of Met (0)-α-hANP was only 25 μg.

While, reduced form of a α-hANP (0.5 mg) was dissolved in 10 mM tris-HCl buffer (1 ml, pH 8.0) containing 6M guanidine hydrochride. The reaction mixture was allowed to stand overnight at ambient temperature. The reaction mixture was determined for RP-HPLC in the same manner as Example 1. Air-oxidation reaction did not entirely proceed and the raw material was quantitatively recovered as unchanged.

From the above result, it is concluded that the intramolecular disulfide bridge is successively formed to produce the oxidized form of α-hANP even under the condition of the highly concentrated salt solution wherein air-oxidation reaction does not entirely proceed.

EXAMPLE 3

Reduced form of somatostatin was oxidized with hydrogen peroxide in the same manner as Example 2 to produce oxidized form of somatostatin (natural type somatostatin wherein intramolecular disulfide bridge was formed). The yield was 93%.

What we claim is:

1. A process for the formation of an intramolecular disulfide bridge in a polypeptide which is characterized by reacting hydrogen peroxide with a cysteine-containing polypeptide to produce a biologically active polypeptide having said intramolecular disulfide bridge, the reaction being carried out at a pH of about 6 to 11, and the molar ratio of hydrogen peroxide to polypeptide being within th range of 1:1 to 100:1.

2. A process for the formation of an intramolecular disulfide bridge in a polypeptide which is characterized by reacting hydrogen peroxide with a cysteine-and methionine-containing polypeptide to produce a biologically active polypeptide having said intramolecular disulfide bridge, the reaction being carried out at a pH of about 6 to 11, and the molar ratio of hydrogen peroxide to polypeptide being within the range of 1:1 to 100:1.

3. The process of claim 1, wherein the cysteine-containing polypeptide is somatostatin.

4. The process of claim 2, wherein the cysteine- and methionine-containing polypeptide is human atrial natriuretic polypeptide.

5. The process of claims 1 or 2, wherein the reaction is carried out at about pH 8~11.

* * * * *